United States Patent [19]

Nowak

[11] Patent Number: 5,244,808
[45] Date of Patent: Sep. 14, 1993

[54] DETECTION OF MARKER DYE IN AGED OR DIRTY MOTOR GASOLINES

[75] Inventor: Anthony V. Nowak, Fullerton, Calif.

[73] Assignee: Atlantic Richfield Company, Los Angeles, Calif.

[21] Appl. No.: 7,425

[22] Filed: Jan. 22, 1993

[51] Int. Cl.$^5$ .............................................. G01N 35/08
[52] U.S. Cl. .................................. 436/56; 436/60; 436/178
[58] Field of Search ................ 436/56, 60, 178; 44/59

[56] References Cited

U.S. PATENT DOCUMENTS

| | | | |
|---|---|---|---|
| 3,976,572 | 8/1976 | Reick | 210/94 |
| 4,049,393 | 9/1977 | Orelup | 44/59 |
| 4,209,302 | 6/1980 | Orelup | 44/59 |
| 4,514,503 | 4/1985 | Orelup | 436/60 |
| 4,717,671 | 1/1988 | Melpolder | 436/39 |
| 4,918,020 | 4/1990 | Nowak | 436/56 |

Primary Examiner—James C. Housel
Assistant Examiner—N. Bhat
Attorney, Agent, or Firm—Michael E. Martin

[57] ABSTRACT

Marker dyes are detected in aged and dirty or "brown" gasolines by passing a sample of gasoline through plural solid phase extraction columns including a first column having a strong anion exchange phase bonded to a silica substrate. A color-forming reagent is added to the first column after elution of the gasoline sample therethrough. The marker dye colored complex and colored bodies not retained on the first column are eluted into a nonpolar solid phase extraction column with methanesulfonic acid and the marker dye colored complex is eluted through the second column and into and through a third column containing unbonded silica. The color bodies of the gasoline will remain on the columns and the marker dye will be detectable at the bottom of the third column as evidenced by a pink color for marker dyes such as Morton International Mortrace MP marker dye and the like.

12 Claims, No Drawings

DETECTION OF MARKER DYE IN AGED OR DIRTY MOTOR GASOLINES

BACKGROUND OF THE INVENTION

1. Field of the Invention

The present invention pertains to a method of detecting the presence of a non-visible marker dye in aged or dirty gasolines using a multi-step solid phase extraction process and elution with a solvent after reacting the marker dye with a color-forming reagent.

2. Background

My U.S. Pat. No. 4,918,020, issued Apr. 17, 1990, discloses and claims a method of detecting the presence of a commercial marker dye known as Marker MP or Mortrace MP and available commercially from Morton International, Inc., Patterson, N.J. Marker MP or Mortrace MP marker dye is used in motor gasolines and similar hydrocarbon fuels as a tracer to detect trademark violation or tax evasion techniques. Although the method set forth in the above-mentioned patent uses solid phase extraction (SPE or sorbent extraction) to selectively extract the dye from gasoline samples, it has been determined that aged gasolines or "dirty" gasolines, that is gasolines which are produced from poor quality refinery processes, cannot normally be adequately analyzed using this technique or the commercial technique provided by Morton International.

However, in accordance with the present invention, a unique solid phase extraction process has been developed which will detect the presence of a marker dye such as Marker MP or Mortrace MP in dirty and aged or "brown" gasolines, in particular. Accordingly, the invention overcomes the above-noted deficiencies in known solid phase extraction methods as well as the commercial liquid/liquid extraction technique wherein both prior art methods include the steps of adding a color-forming reagent to the extractant to form a colored complex and then determining the color intensity of the colored complex as an indication of the concentration of the marker dye.

A somewhat related discovery is disclosed in my patent application entitled "Method for Detecting a Marker Dye in Aged Petroleum Distillate Fuels" filed of even date herewith Ser. No. 08/007,412 pending.

SUMMARY OF THE INVENTION

The present invention provides an improved method for detecting the presence of a marker or tracer dye in aged, dirty or otherwise substantially discolored motor gasolines.

In accordance with one aspect of the present invention, the marker dye is separated substantially from the remainder of a sample of gasoline suspected of containing the dye by passing the sample through a solid phase extraction (SPE) column, particularly a column which contains a chemically selective moiety bonded to a silica substrate and which comprises a strong anion exchange phase (SAX).

In accordance with another aspect of the present invention, after adding a color-forming reagent to the SAX column, an eluant liquid is added to the column and the eluant is eluted into a second solid phase extraction (SPE) column, particularly one which is strongly nonpolar, to extract further ones of the colored complexes which have formed in the gasoline.

Still further in accordance with the present invention, a solvent is added to the nonpolar SPE column and eluted through the nonpolar column and through an SPE column which attracts polar compounds, such as an unbonded silica solid phase extraction (SPE) column. The remaining polar color-forming agents are extracted onto the silica SPE column while the colored marker dye, if present, will be observed on the lower portion of the silica SPE column as indicated by a pink substance. The colored substance appearing at the bottom of the silica SPE column may be eluted into a spectrophotometer cell and scanned to confirm the presence of the particular marker dye.

Accordingly, a unique solid phase extraction process is provided wherein both polar and nonpolar colored complexes are removed or distinguished from the reacted marker dye which, after retention of the colored complexes on the respective columns, the marker dye can be identified visually.

Those skilled in the art will recognize that the method of the present invention is relatively uncomplicated, easy to perform rapidly, substantially independent of operator variances, and even in routine application, provides for detecting the presence of a marker dye in motor gasoline at very low concentrations. The extraction process is selective, reproducible and efficient, resulting in a clear separation of the marker dye from the gasoline compositional matrix and from other additives usually found in motor gasoline. The process can be implemented in the field without the use of large quantities of volatile or hazardous materials or complicated equipment. The solid phase extraction columns are easily disposed of and large quantities of volatile fuels are not required for the detection process.

Those skilled in the art will recognize the above-described features and advantages of the present invention together with other superior aspects thereof upon reading the detailed description which follows.

DESCRIPTION OF PREFERRED EMBODIMENTS

U.S. Pat. No. 4,209,302, issued Jun. 24, 1980 to Orelup, discloses marker dyes which can be usefully employed and detected in accordance with the present invention. The disclosure of the '302 patent is hereby incorporated by reference. The disclosure of my U.S. Pat. No. 4,918,020 is also hereby incorporated by reference. Generally speaking, the dyes disclosed in the Orelup '302 patent form a colored complex when reacted with a color-forming reagent. Diazotized aromatic amines are suitable color-forming reagents. Preferably, the color-forming reagent is solubilized, stored and used in glacial acetic acid and is available from the source of the Marker MP or Mortrace MP dye under the designation Reagent DII.

The solid phase extraction columns utilized in accordance with the present invention comprise column packing disposed in a suitable vessel and through which the sample of aged or dirty gasoline is passed. The packing is mostly silica powder to which has been applied a moiety which is chemically selective for the marker dye and for the color bodies in the aged or "brown" gasoline. The Marker MP or Mortrace MP dye reacts with a moiety covalently bonded to the silica which includes a strong anion exchange (SAX) phase such as a quaternary amine functional group.

A preferred method is to pass the sample of aged or dirty gasoline containing the marker dye through the bed of the SAX column packing to extract the dye and certain color bodies from the sample. The marker dye is generally present in motor gasoline at a level in the range of about 0.50 to 5.0 parts per million (ppm) based on weight. It is contemplated that the method may also be applied to fuel samples containing even lower levels of marker dyes which would require passing increasingly larger samples through the extraction column. After separation in the SAX SPE column, a rinsing solvent is passed through the column to remove residual quantities of the fuel sample. At this point a prescribed quantity of the color-forming reagent is added to the SAX SPE column and allowed to react.

The steps in the process just described are those set forth in U.S. Pat. No. 4,918,020. In accordance with the present invention, it has been determined that, by eluting the material on the column packing of the SAX SPE column with a first solvent comprising two percent methane-sulfonic acid into a second SPE column followed by eluting the material which has deposited on the second SPE column with a second solvent into a strongly polar SPE column such as an unbonded silica type column, a substantial amount of the color bodies in the aged gasoline are separated from the marker dye to permit visual detection of the dye in the third column.

The second SPE column is preferably a highly nonpolar column with a silica substrate and an octadecyl (C18H17) chemical functionality residing thereon. A convenient way of performing the novel steps in passing the sample through the second and third columns is to stack these columns together and elute the material extracted from the SAX SPE column through the second and third columns seriatim.

Elution with the second solvent will result in elution of the reacted marker dye through both columns and which will be visible in the lower portion of the unbonded silica SPE column as a pink band. The pink colored substance may be further eluted from the silica SPE column into a spectrophotometer cell and scanned in a prescribed range of wavelengths to verify an absorbance maximum at about 530 nanometers (nm) to confirm the presence of the above-mentioned type of marker dye.

The above-mentioned method, surprisingly, has been successful in detecting the presence of dyes comprising 1-(amino)-3-(alpha or beta naphthylamino)-propanes when these dyes have been reacted with a proprietary coloring agent. Such detection of marker dyes in aged or "brown" gasolines could not be detected with liquid-liquid extraction techniques or with a SAX solid phase extraction column alone. A detailed procedure will now be described.

EXAMPLE I

The following SPE separation columns are used in this procedure and are available commercially from Varian Separation Products, Harbor City, Calif. The SAX separation column is preferably of the type mentioned hereinbefore and is available from Varian Separation Products under their catalog number 210-2044. The nonpolar (C18H17) SPE column is available from the same source as their catalog number 1210-2028. Lastly, the polar, unbonded silica SPE column is available from Varian Separation Products as their catalog number 1210-2037. preferably, a column adaptor, available from Varian Separation Products, is used to connect the so-called C18 or nonpolar column with the polar or unbonded silica column.

The SAX column is preferably conditioned with 2.0 ml of a pH2 buffer solution using positive pressure to force the buffer solution through the column. Preferably, a 20.0 ml reservoir is attached to the SAX column and a 50.0 ml sample of the gasoline to be analyzed is eluted slowly through the column, preferably using a vacuum manifold. After extraction of the sample, the SAX column is allowed to air dry for two minutes while connected to the vacuum manifold, in operation.

The SAX column is then rinsed with two separate rinses of 2.0 ml each of hexane.

The SAX column is again allowed to air dry for two minutes on the vacuum manifold after which the manifold is de-energized.

The Morton Reagent DII is then added to the SAX column in the amount of 200 µl and the reaction is allowed to progress for about two minutes.

One ml of two percent methane-sulfonic acid is then added to the SAX column and is eluted into the C18 column with positive pressure. A 30 ml disposable plastic syringe, attached firmly to the top of the SAX column, may be used for the displacement process.

The C18 and unbonded silica columns are then stacked together using the column adaptor while the fluid eluted into the C18 column is then eluted through the C18 column and through the unbonded silica column with positive pressure. The stacked columns are then eluted with one ml of dichloromethane until orange coloration on the columns is removed. An orange band will remain at the top of the column. Coloring observation may be confirmed by comparing the test columns with unused columns of the same type. While removing the orange coloration from the columns, observe the lower section of the unbonded silica column for a pink color indicating the presence of the marker dye referenced herein. Confirmation of the pink coloring may be obtained by comparing the test column with an unused column of the same type.

Further confirmation of the presence of the marker dye may be obtained by eluting the pink coloration with the dichloromethane solvent into a spectrophotometer cell and scanning the substance with a spectrophotometer in the range of 360 nm to 720 nm. An absorbance maximum at about 530 nm will confirm the presence of the Morton Marker MP or Mortrace MP dye.

Although a preferred method in accordance with the invention has been described herein, those skilled in the art will recognize that certain substitutions and modifications may be made without departing from the scope and spirit of the invention as recited in the appended claims.

What is claimed is:

1. A method for determining the presence of a marker dye in aged or darkened motor gasoline comprising the steps of:
    passing a sample of said motor gasoline containing said marker dye through a first column having a packing to selectively retain the marker dye on the column packing together with certain color bodies in said sample to thereby substantially separate said color bodies and said marker dye from said sample;
    reacting the separated marker dye with a color-forming reagent to form a colored complex;
    removing said color complex of said marker dye and certain color bodies from said first column and placing said colored complex of said marker dye and said color bodies on a second column having a relatively nonpolar packing;

removing said colored complex of said marker dye from said second column; and placing said colored complex of said marker dye on a third column having a substantially polar packing therein until said colored complex of said marker dye is visually observed on said third column.

2. The method set forth in claim 1 wherein:
the packing of said first column includes a strong anion exchange moiety.

3. The method set forth in claim 1 wherein:
said second column includes a packing having an octadecyl moiety.

4. The method set forth in claim 1 wherein:
said third column includes unbonded silica packing.

5. The method set forth in claim 1 wherein:
said colored complex of said marker dye is eluted from said first column by methane-sulfonic acid.

6. The method set forth in claim 1 wherein:
said colored complex of said marker dye is eluted through said second column with dichloromethane.

7. The method set forth in claim 1 including the step of:
rinsing said first column packing with a rinse solvent before reacting said marker dye retained on said first column with said color-forming reagent.

8. The method set forth in claim 7 wherein:
said rinse solvent is hexane.

9. The method set forth in claim 7 including the step of:
air drying said packing of said first column prior to adding said color-forming reagent.

10. The method set forth in claim 1 including the step of:
conditioning said first column with a buffer having a pH of 2.

11. A method for determining the presence of a marker dye in aged or darkened motor gasoline comprising the steps of:

providing a first solid phase extraction column including a packing having a strong anion exchange phase, a second column having a packing including an octadecyl moiety bonded on a silica substrate and a third column having a packing which includes unbonded silica;

passing a sample of said motor gasoline containing said marker dye through said first column to selectively retain said marker dye together with certain color bodies in said sample on said first column to thereby substantially separate said marker dye and said certain color bodies from said sample;

rinsing said packing of said first column with a solvent to remove residue of said sample;

reacting said marker dye with a color-forming reagent to form a colored complex;

eluting at least said colored complex of said marker dye and certain color bodies from said first column with methane-sulfonic acid;

passing the eluent of said methane-sulfonic acid, said colored complex of said marker dye and said certain color bodies onto a second column having a relatively non-polar packing characterized by an octadecyl moiety on a silica substrate; and eluting said colored complex of said marker dye from said second column onto said third column with dichloromethane until an orange color of a major portion of the packing of said third column is removed therefrom and until a lower section of the packing of said third column exhibits a pink color to confirm the presence of said marker dye.

12. The method set forth in claim 11 including the step of:
eluting the pink-colored substance from the packing of said third column into a spectrophotometer cell and scanning with a light signal having a wavelength which will detect an absorbance maximum at about 530 nanometers to confirm the presence of said marker dye.

* * * * *